(12) United States Patent
McDonald et al.

(10) Patent No.: US 6,979,318 B1
(45) Date of Patent: Dec. 27, 2005

(54) CATHETER INTRODUCER

(75) Inventors: David McDonald, Medway, MA (US); Christine Willy, Medford, MA (US)

(73) Assignee: LeMaitre Vascular, Inc., Burlington, MA (US)

( * ) Notice: Subject to any disclaimer, the term of this patent is extended or adjusted under 35 U.S.C. 154(b) by 99 days.

(21) Appl. No.: 10/265,823

(22) Filed: Oct. 7, 2002

(51) Int. Cl.[7] .......................... A61M 5/178; A61M 5/00
(52) U.S. Cl. ........................ 604/158; 604/239; 604/264
(58) Field of Search .............................. 604/158, 159, 604/160, 161, 162, 264, 239, 272–274, 164.01

(56) References Cited

U.S. PATENT DOCUMENTS

| | | | |
|---|---|---|---|
| 4,795,446 A | * 1/1989 | Fecht | 604/264 |
| 4,842,585 A | 6/1989 | Witt | |
| 5,100,390 A | * 3/1992 | Lubeck et al. | 604/158 |
| 5,167,645 A | 12/1992 | Castillo | 604/272 |
| 5,183,470 A | 2/1993 | Wettermann | 604/281 |
| 5,295,980 A | * 3/1994 | Ersek | 604/272 |
| 6,186,987 B1 | 2/2001 | Grooters | |
| 6,254,578 B1 | * 7/2001 | Grooters et al. | 604/264 |

* cited by examiner

Primary Examiner—Michael J. Hayes
(74) Attorney, Agent, or Firm—McDermott Will & Emery LLP

(57) ABSTRACT

A catheter introducer includes a tube having a proximal end, a distal end and a lumen extending therethrough along a longitudinal axis of the tube for accommodating a catheter traveling along a longitudinal axis of the tube and a head portion coupled to the distal end of the tube. The head portion includes an aperture in fluid communication with the lumen at a proximal end thereof and a tip at a distal end thereof, an exterior surface extending from the proximal end thereof to an opening of the head portion along a first portion of the head portion and extending from the proximal end thereof to the tip along an opposing portion of the head portion and an interior surface extending from the aperture to the opening of the head portion along the first portion of the head portion and extending from the aperture toward the tip along the opposing portion of the head portion. The exterior surface circumferentially tapers from the proximal end to the distal end and the interior surface forms a channel for receiving a catheter passing through the lumen and the aperture, the channel being concave along at least one axis.

20 Claims, 21 Drawing Sheets

CATHETER INTRODUCER

FIELD OF THE INVENTION

The invention relates generally to medical devices and more particularly to catheter introducing devices.

BACKGROUND OF THE INVENTION

During surgical procedures, catheter introducers are often used to provide a conduit for passage of catheters and other relatively long, thin and flexible medical devices, for example, guide wires, into lumens in a patient. For example, in cholangiography procedures, an introducer is used to establish a guide channel to permit advancement of a catheter to an incision in the wall of the cystic duct of the gallbladder. The catheter is introduced through the introducer, under control of the surgeon, and is extended out of the introducer. The distal tip of the catheter is manipulated by the surgeon into the incision in the cystic duct, and navigated by the surgeon through the lumen of the cystic duct forward and through the valve of Heister. During this procedure, the valves or other obstructions can inhibit the catheter's advancement in the duct.

Prior art catheter introducers include a cannula and a hub mounted on a proximal end of the cannula. The cannula is generally straight in profile, and the catheter passes through the distal end of the cannula along the same axis as the cannula. During the surgical procedure, the surgeon typically approaches the cystic duct at some oblique angle to its longitudinal axis. Depending on the approach angle, a straight introducer may direct the catheter directly into the opposite wall of the duct, and may require pushing against the back wall of the duct in order to bend the catheter and direct it into the lumen of the duct. The elasticity of the duct wall makes such a procedure very difficult.

Some prior art introducers utilize a curved distal end to direct the catheter into the cystic duct. The curved introducers represent an improvement over the straight introducers, but still do not provide the support and control necessary for optimized catheter insertion. In general, both straight and curved introducers share a common problem. Laparoscopic procedures are difficult to execute because the surgeon is operating with instruments on an extended lever arm. For a cholangiography, a catheter must be inserted into a small incision in the cystic duct, the narrowest of the extra-hepatic ducts, which is generally 3 to 7 mm in diameter. With existing cholangiography procedures, the surgeon must be able to transmit navigation motions to insure that the catheter is properly inserted into the incision in the duct. Existing introducers do not have a tip which is optimized for providing access of the catheter to the cystic duct. While existing introducers may enable the surgeon to navigate the end of the catheter proximate the incision, they still require that the surgeon enter the incision with the end of the catheter, which can be difficult, given the necessary flexibility of the catheter, the diameter of the catheter and the typical dimensions of the incision.

What is needed is an improved catheter introducer which may be easily inserted into the cystic duct, and may be easily manipulated for laparoscopic cholangiograms.

SUMMARY OF THE INVENTION

The present invention provides a catheter introducer device including a tapered tip which facilitates insertion of the catheter into the cystic duct.

A catheter introducer includes an elongated tube extending from a proximal end to a distal end along a longitudinal axis and a direction translation device. The tube has a lumen for accommodating a catheter. The direction translation device, which may include a scoop-shaped, spoon-shaped or straight head portion, extends from the distal end of tube. The head portion includes an upper surface in connection with the lumen, a lower surface extending from the outer surface of said tube, a distal tip, and a catheter receiving portion formed between the lumen and the tip. The catheter receiving portion is defined by a two-axis concave surface extending from the interior surface of central lumen to the distal tip. The distal tip may be pointed, bill-shaped, or channeled. The concave surface of the catheter receiving portion and the distal tip form a path for guiding an inserted catheter, such that a lead end of the catheter traveling through the lumen contacts the concave surface of the catheter receiving portion upon exiting the lumen and is forced to travel in a direction oblique to the longitudinal axis. For properly guiding the catheter to a desired direction, and for properly placing the catheter in a duct, the catheter receiving portion may be constructed substantially straight, or slightly curved, or substantially curved corresponding to the shape of the duct or the requirement of a surgery procedure.

In one embodiment, the protrusion is scoop-shaped. The protrusion has a width, which monotonically decreases from the distal end of the tube to the distal tip of the protrusion. In another embodiment, the width of the protrusion monotonically decreases from a point between the distal end of the tube and the distal tip of the protrusion to the distal tip of the protrusion.

In yet another embodiment, the protrusion is spoon-shaped. The spoon-shaped protrusion may have a first width at the base and a second width at an intermediate point between the base and the tip, the second width being greater than the first width. The spoon-shaped protrusion may taper in width from the intermediate point to the tip. The catheter receiving portion of the spoon-shaped protrusion may include a one- or two-axis concave surface for translating a direction of travel of the catheter within the lumen which is parallel to a longitudinal axis of the tube to a direction of travel outside of the lumen which is oblique to the longitudinal axis.

In yet another embodiment, the protrusion is substantially straight. The protrusion extends from the distal end of the tube. The straight protrusion design is adapted for introducing an inserted catheter to a direction parallel to the longitudinal axis of the tube.

The head portion may be constructed within planes tangent to the outer surface of the tube. The smaller profile design of the head portion allows insertion of the head portion through the incision in the cystic duct, and placement within it. Following such insertion, a catheter may be inserted into the introducer from the proximal end, extended out from the head portion and guided into the lumen of the cystic duct. The curved design of the protrusion also provides good support for the catheter if it encounters resistance from valves or other obstructions.

The small profile design of the protrusion also makes it easier for the introducer to be inserted along the lumen of the cystic duct. During operation, electro-cauterization may be utilized to stop any bleeding at the incision site. This may cause the duct tissue to shrink, or a buildup of dead tissue to partially obstruct the lumen of the cystic duct. The leading edge of the tip can be used to pass through this narrowed incision, and then can be positioned for directing catheter insertion in the duct.

According to another aspect of the invention, a catheter introducer includes a tube having a proximal end, a distal end and a lumen extending therethrough along a longitudinal axis of the tube for accommodating a catheter traveling along a longitudinal axis of the tube and a head portion coupled to the distal end of the tube. The head portion includes an aperture in fluid communication with the lumen at a proximal end thereof and a tip at a distal end thereof, an exterior surface extending from the proximal end thereof to an opening of the head portion along a first portion of the head portion and extending from the proximal end thereof to the tip along an opposing portion of the head portion and an interior surface extending from the aperture to the opening of the head portion along the first portion of the head portion and extending from the aperture toward the tip along the opposing portion of the head portion. The exterior surface circumferentially tapers from the proximal end to the distal end and the interior surface forms a channel for receiving a catheter passing through the lumen and the aperture, the channel being concave along at least one axis.

The interior surface may be curved along a radius of curvature. The radius of curvature may be a nonzero value or infinite. The channel may be concave along two axes. The exterior surface along the first portion of the head portion may completely surround the opening, thereby forming a protruding portion at the tip. The protruding portion may include a flat bill or a pointed tip. The head portion may remain within planes which are tangent to an outer surface of the tube. The channel may deflect the catheter from traveling along the longitudinal axis to a direction oblique to the longitudinal axis as the catheter is directed through the head portion. The head may be constructed such that the catheter exits the opening at an angle which is between zero and thirty degrees with respect to the longitudinal axis. The head portion may be constructed such that the longitudinal axis of the tube passes through the opening or such that the longitudinal axis of the tube intersects the channel. A line connecting the first portion of the exterior surface at the opening and the tip may lie in a plane which is oblique with respect to the longitudinal axis.

The present invention also provides a method of using the improved catheter introducer. During operation, the introducer is first guided towards the cystic duct. The head portion of the introducer is then inserted into the incision in the duct, and positioned so that the concave channel of the direction translation device is substantially orthogonal to the longitudinal axis of the duct. The catheter is then advanced down the introducer until it extends out of the head portion and is guided into the lumen of the duct.

DESCRIPTION OF THE FIGURES

Other advantages and novel features will be set forth in the detailed description, taken in conjunction with the accompanying drawings, in which:

FIGS. 16A–16D are various views of another embodiment of a catheter introducer scoop-shaped head portion according to the present invention

DETAILED DESCRIPTION OF THE PREFERRED EMBODIMENT

Figure 1:
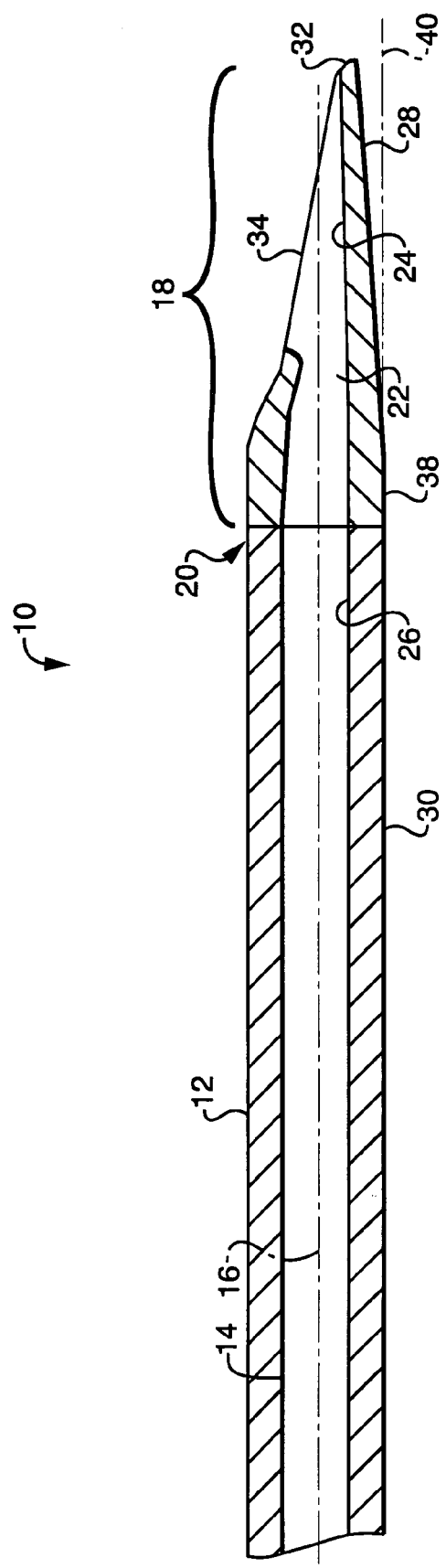
FIG. 1 is a cross-sectional view of a catheter introducer in accordance with the present invention.
Figure 2A:
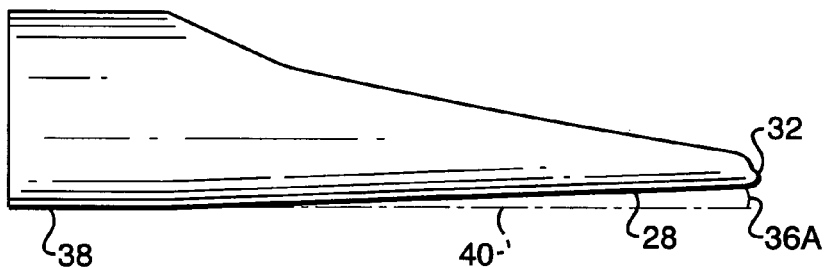
FIGS. 2A–2C are various views of one embodiment of a catheter introducer straight head portion according to the present invention.
Figure 2B:
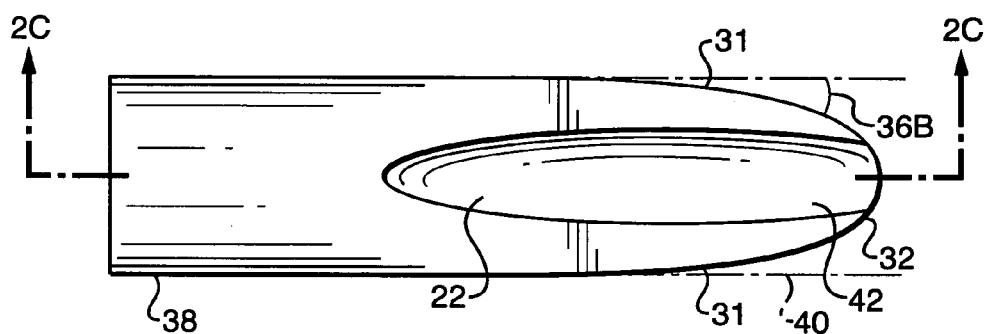
Figure 2C:
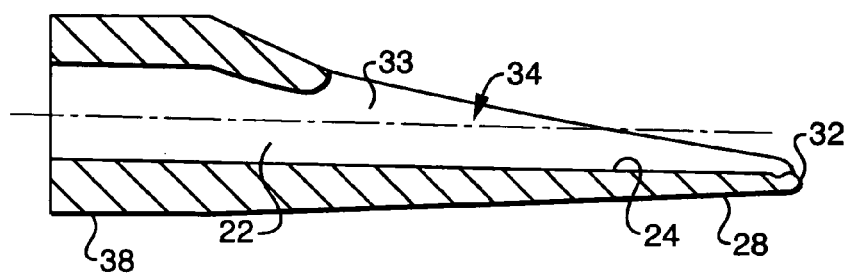

The present invention is directed to a catheter introducer including a tapered tip which facilitates the insertion of the introducer into an incision in a duct, thereby enabling a surgeon to direct the catheter into the duct to the desired location. FIG. 1 shows a cross-sectional diagram of one embodiment 10 of the invention. As shown in FIG. 1, the introducer 10 includes a tube 12 having a lumen 14 along a longitudinal axis 14. A head portion 18 extends from a distal end 20 of the tube 12. As shown in FIGS. 2A–2C, in which FIG. 2A is a side view of the head portion 18 of FIG. 1, FIG. 2B is a top view of the head portion 18 of FIG. 1 and FIG. 2C is the same cross-sectional view of the head portion 18 of FIG. 1, taken along line 2C—2C of FIG. 2B. As shown in these figures, head portion 18 is extends generally along the longitudinal axis 16 and includes a lumen extension portion 22 having an interior surface 24 which extends from the interior surface 26 of lumen 14 of tube 12. Head portion 18 further includes an exterior surface 28 which extends from the exterior surface 30 of the tube 12. As shown in FIGS. 1 and 2C, the interior surface 24 and the exterior surface 28 converge toward each other to form a tip 32 which, as is described in more detail below, is used to facilitate the insertion of the head portion 18 into an incision in the cystic duct. Lumen extension portion 22 of the head portion 18 terminates at an opening 34 of the head portion 18, which opening 34 enables a catheter passing through the lumen 14 and lumen extension portion 22 to exit the head portion proximate the tip 32 at an angle which is relatively acute with respect to the relative plane within which the opening 34 lies. As shown in FIGS. 1 and 2A–2C, head portion 18 tapers from its proximal end 38, adjacent distal end 20 of tube 12 to the tip 32. This taper occurs along outer sidewalls 31 as well as along exterior surface 28 with respect to two orthogonal planes which intersect along the longitudinal axis 16 of tube 12. As a result, exterior surface 28 tapers circumferentially inwardly from planes tangential to the exterior surface 30 of tube 12, the tangential planes being shown in the figures by dashed line 40. The amount of taper, indicated by reference numerals 36a and 36b, may vary, depending on the particular application and procedural requirements. While the exterior surfaces of the head portion 18 taper as described and shown, the interior surface 24 of the head portion 18 remains parallel to the longitudinal axis 16 such that the direction of travel of the catheter through the head portion 18 remains along the longitudinal axis 16.

In use, a catheter (not shown) is directed through the lumen 14 of the tube 12 into a position in which the distal end of the catheter is located proximate the distal end 20 of the tube 12. The introducer 10 is brought into close proximity to an incision in the cystic duct and the surgeon inserts the tip 32 of head portion 18 into the incision. Depending on the size of the incision relative to the diameter of the head portion 18, the surgeon may insert as much as the entire head portion 18 into the incision, thereby aligning the distal end of the catheter with the incision or, preferably inserting the distal end of the catheter into the incision. With the head portion 18 in such a position, the surgeon is then able to navigate the catheter into the cystic duct and through any obstruction within the duct, with the aid of the head portion 18 and particularly tip 32.

Figure 3A:
FIGS. 3A–3C are various views of another embodiment of a catheter introducer straight head portion according to the present invention.
Figure 3B:
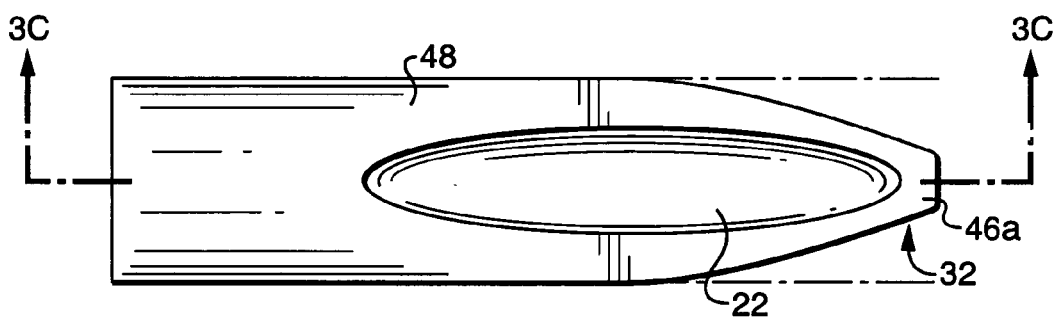
Figure 3C:
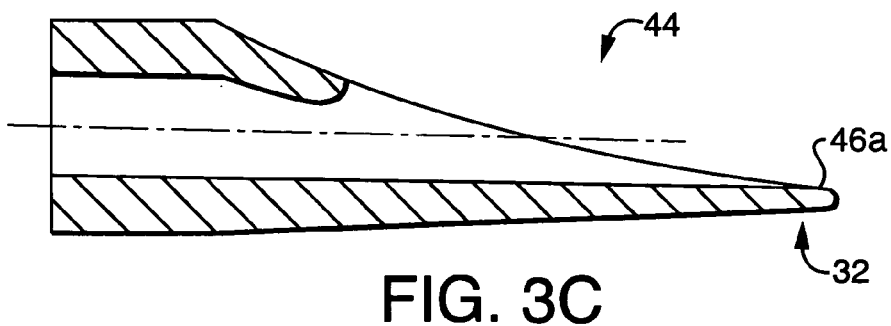
Figure 4A:
FIGS. 4A–4C are various views of another embodiment of a catheter introducer straight head portion according to the present invention.
Figure 4B:
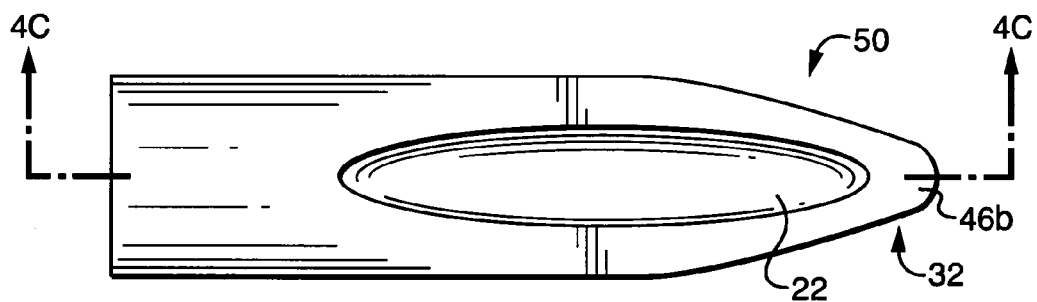
Figure 4C:
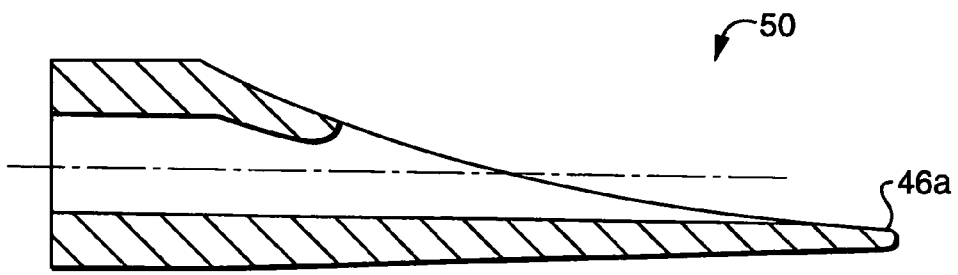
Figure 5A:
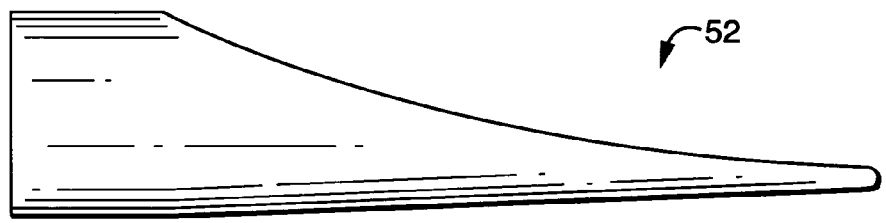
FIGS. 5A–5C are various views of another embodiment of a catheter introducer straight head portion according to the present invention.
Figure 5B:
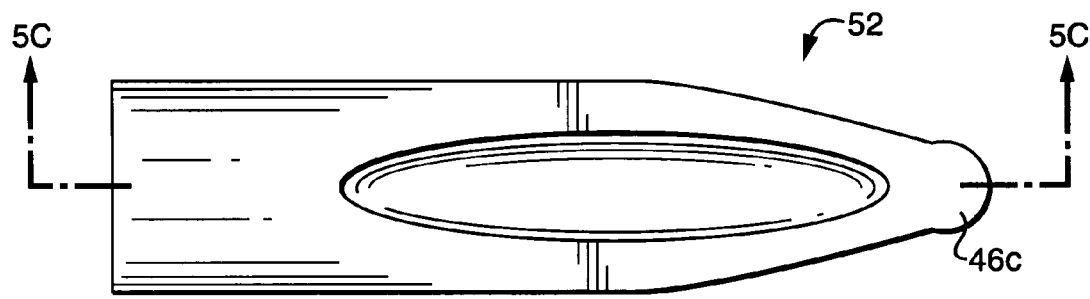
Figure 5C:
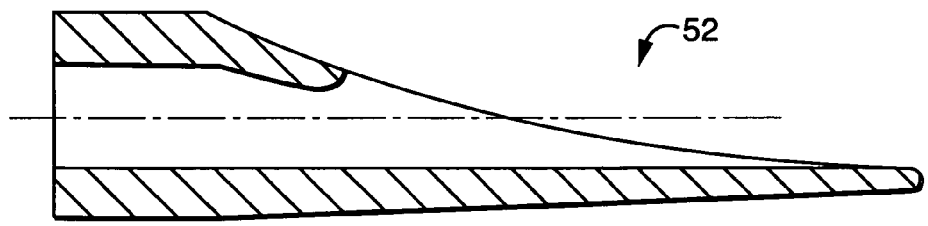
Figure 6A:
FIGS. 6A–6C are various views of another embodiment of a catheter introducer straight head portion according to the present invention.
Figure 6B:
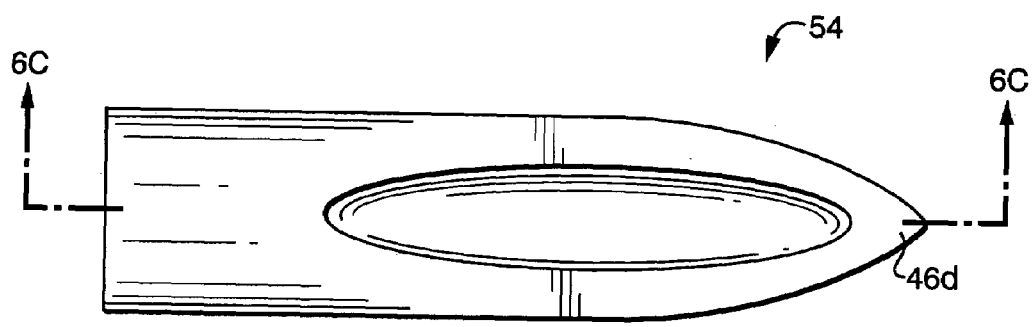
Figure 6C:
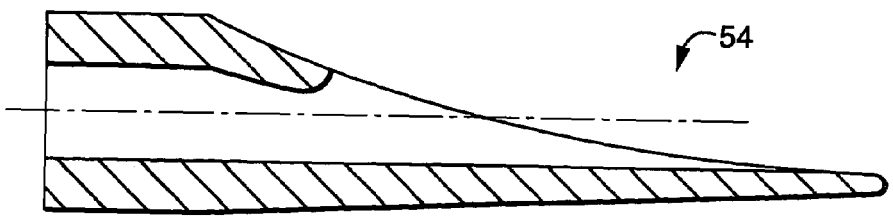
Figure 7A:
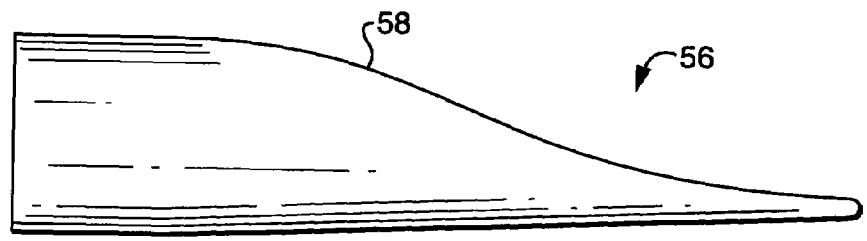
FIGS. 7A–7C are various views of another embodiment of a catheter introducer straight head portion according to the present invention.
Figure 7B:
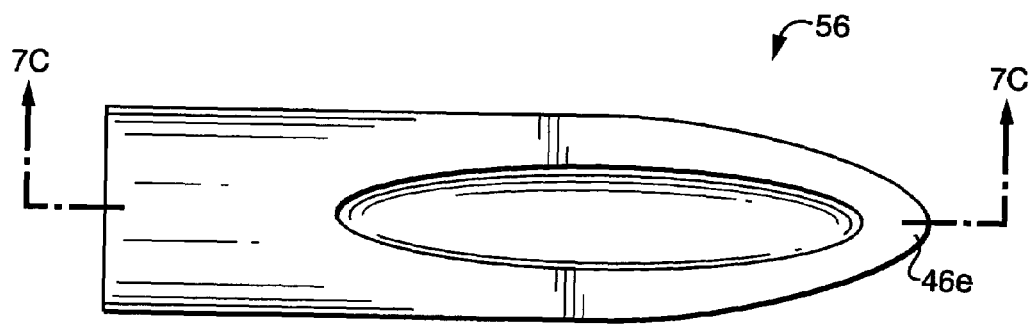
Figure 7C:
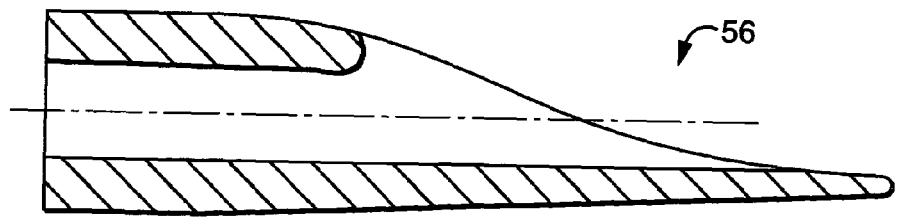

As shown in FIGS. 2A–2C, this embodiment includes a channel 42 formed between the lower interior surface 24 which extends from the proximal end 38 of the head portion 18 to the tip 32 and interior sidewalls 33 and which, by the nature of the interior surface of the lumen, is concave around the longitudinal axis. The catheter rides within this channel as it is directed out of the opening 34 and through the duct. FIGS. 3A–3C show another embodiment 44 of the straight head portion 18. This embodiment is similar to that shown in FIGS. 2A–2C, with the exception that the channel 22 terminates at a lip 46a of the tip 32. In this embodiment, lip 46a is formed to be continuous with exterior portion 48 of the head portion.

Shown in FIGS. 4–7 are various configurations of the lip 46. Each configuration is advantageous in enabling the surgeon to insert the tip and head portion into the incision in the cystic duct and through the valves and other obstructions in the duct that may be encountered by the surgeon during the procedure, while reducing the chance of causing any damage within the duct with the tip of the head portion. FIGS. 4A–4C show an embodiment 50 of the straight head portion, including a lip 46b which is in the form of a flat bill shape. FIGS. 5A–5C show an embodiment 52 of the straight head portion, including a lip 46c which is in the form of an extended flat bill shape. FIGS. 6A–6C show an embodiment 54 of the straight head portion, including a lip 46d which is in the form of a pointed tip. FIGS. 7A–7C show an embodiment 56 of the straight head portion, including a lip 46e which is in the form of a flat bill shape and which includes a more rounded transition between the sidewalls and the top portion of the outer surface 24.

Figure 8A:
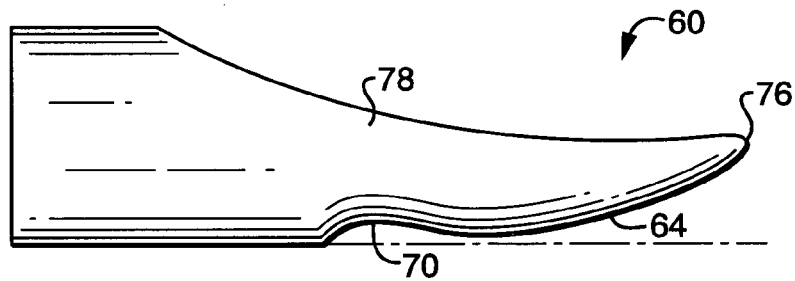
FIGS. 8A–8D are various views of another embodiment of a catheter introducer spoon-shaped head portion according to the present invention.
Figure 8B:
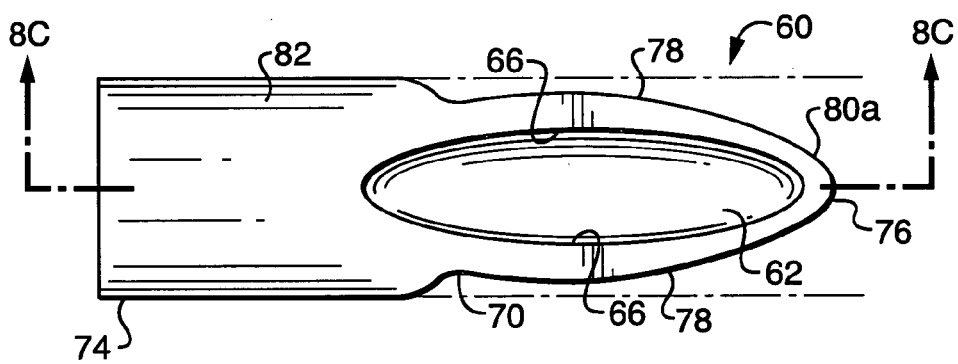
Figure 8C:
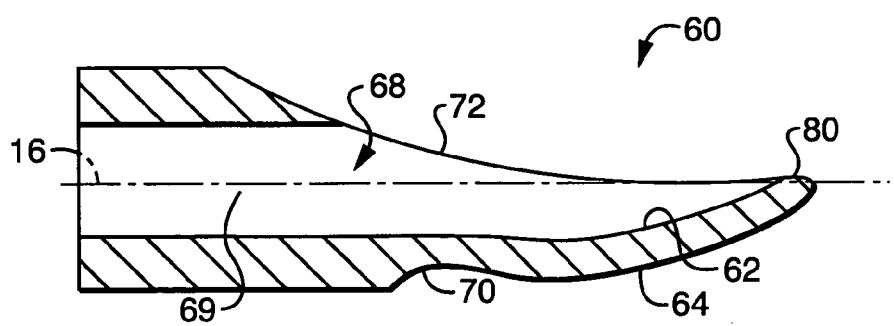
Figure 8D:
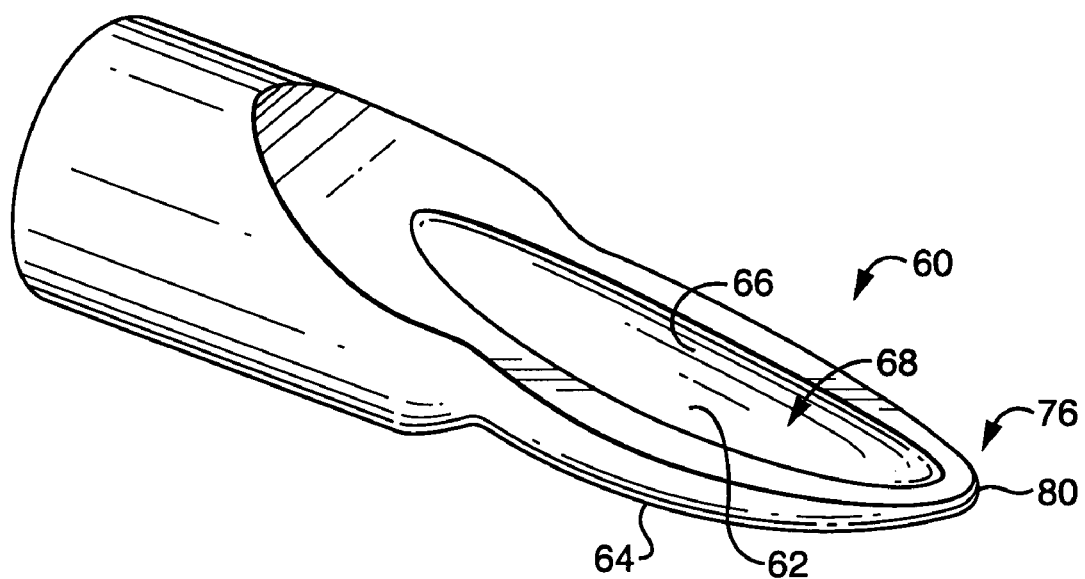

In another embodiment of the present invention, the head portion may be curved with respect to the longitudinal axis to enable the interior surface of the head portion to impart a deflecting force on the catheter as it is directed through the head portion and beyond the opening therein. FIGS. 8A–8D show such an embodiment 60, wherein FIG. 8A is a side view of the head portion 60, FIG. 8B is a top view of the head portion, FIG. 8C is a cross-sectional view of the head portion 60, taken along line 8C—8C in FIG. 8B and FIG. 8D is a three-dimensional perspective view of the head portion 60. As shown in FIGS. 8A–8D, head portion 60 is generally spoon-shaped, wherein interior surface 62 and the exterior surface 64 are curved upwardly with respect to the longitudinal axis 16. The combination with sidewalls 66 and interior surface 62 result in a channel 68 that is concave in two-dimension, both along the longitudinal axis 16 and around it. This feature is particularly shown in FIG. 8D. Similarly to the head portion 18, head portion 60 tapers from its proximal end 74, adjacent distal end 20 of tube 12 to the tip 76. This taper also occurs along outer sidewalls 78 as well as along exterior surface 64 with respect to two orthogonal planes which intersect along the longitudinal axis 16 of tube 12. Head portion 60 may also include a circumferential shoulder portion 70, for facilitating the taper described above. In the spoon-shaped configuration shown in FIGS. 8A–8D, the tip 76 includes a lip 80a that is continuous with exterior portion 82 of the head portion 60.

Lumen extension portion 69 of the head portion 60 terminates at an opening 72 of the head portion 60, which opening 72 enables a catheter passing through the lumen 14 and lumen extension portion 69 to exit the head portion proximate the tip 76 at an angle which is relatively acute with respect to the relative plane within which the opening 72 lies.

In use, when the tip 76 of head portion 60 is inserted into the incision and the catheter is directed through lumen 14 into channel 68, it contacts surface 62 and is deflected laterally with respect to the longitudinal axis 16. This lateral deflection facilitates navigation of the catheter through the duct by the surgeon by enabling the surgeon to laterally move the catheter within the duct by laterally moving the head portion of the introducer.

Figure 9A:
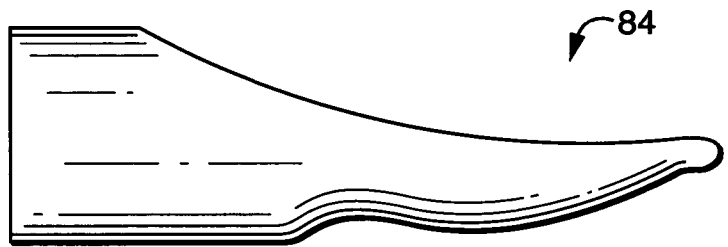
FIGS. 9A–9C are various views of another embodiment of a catheter introducer spoon-shaped head portion according to the present invention.
Figure 9B:
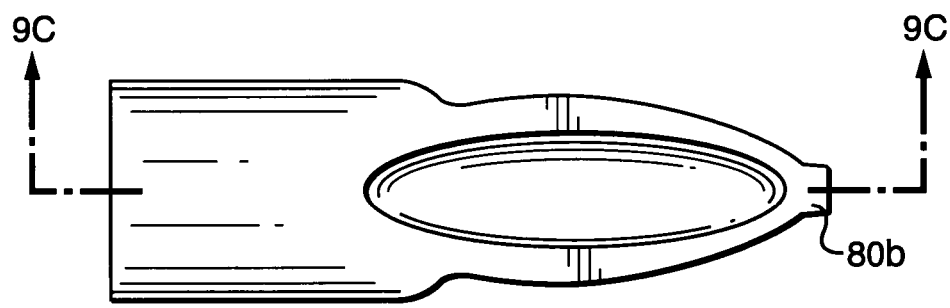
Figure 9C:
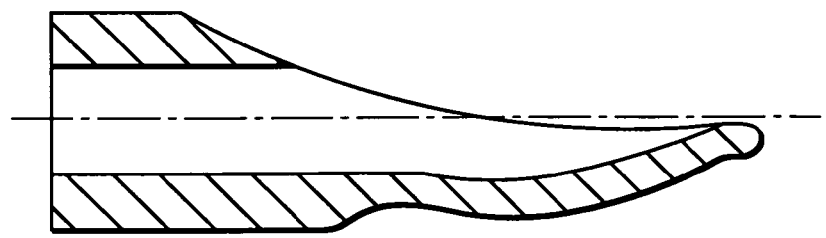
Figure 10A:
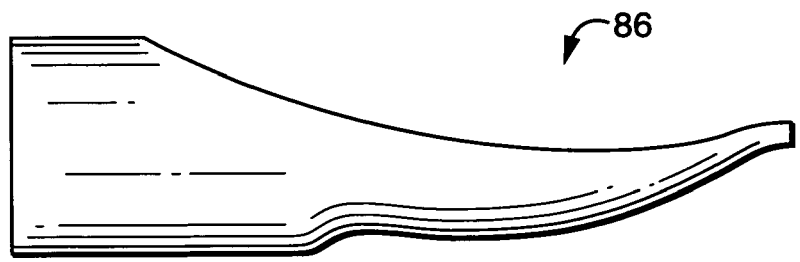
FIGS. 10A–10C are various views of another embodiment of a catheter introducer spoon-shaped head portion according to the present invention.
Figure 10B:
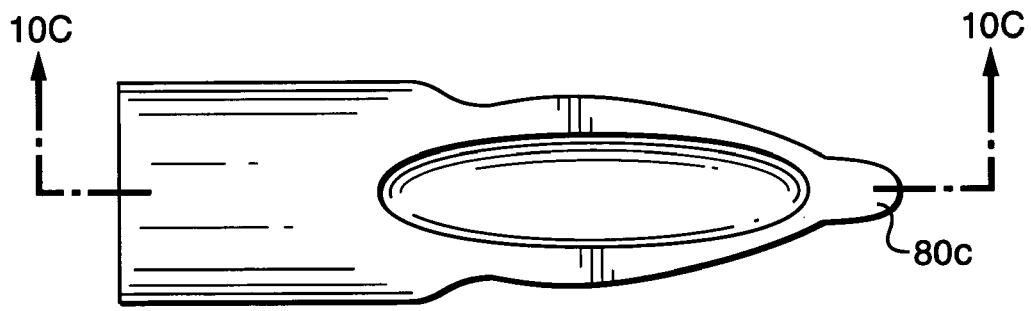
Figure 10C:
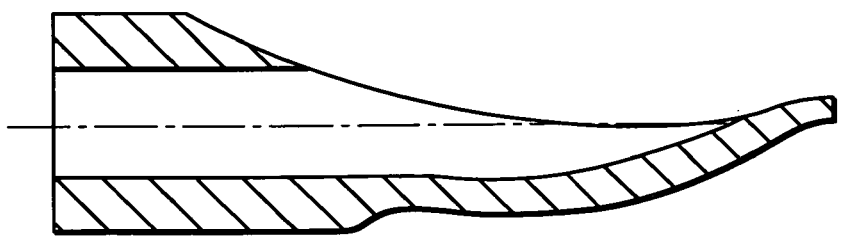
Figure 11A:
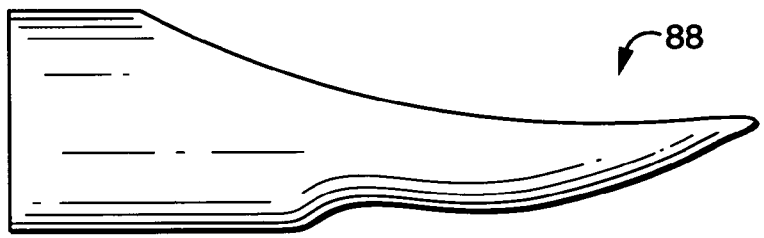
FIGS. 11A–11D are various views of another embodiment of a catheter introducer spoon-shaped head portion according to the present invention.
Figure 11B:
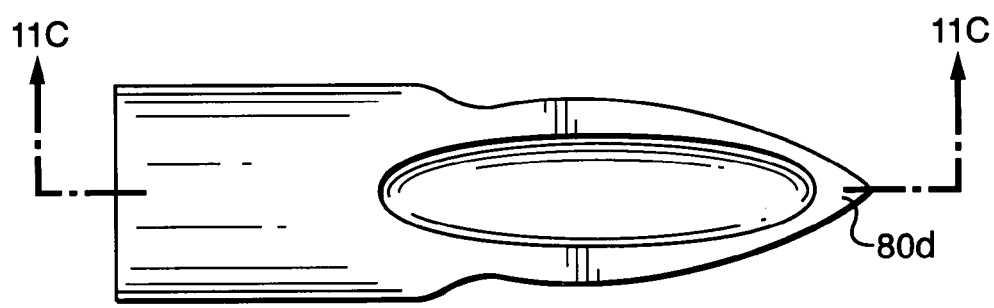
Figure 11C:
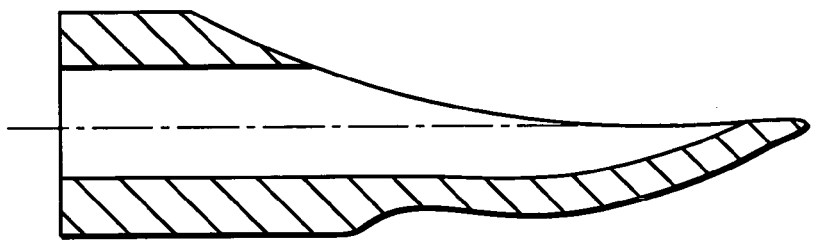
Figure 11D:
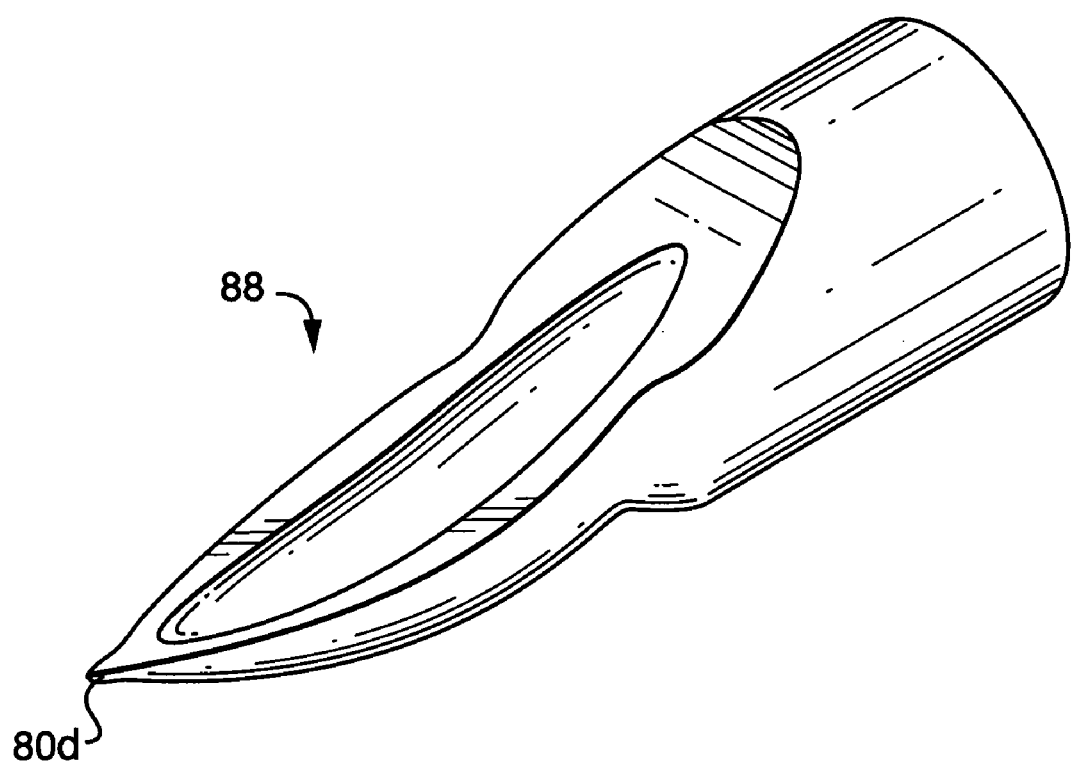

Shown in FIGS. 9–11 are various configurations of the lip 80. Each configuration is advantageous in enabling the surgeon to insert the tip and head portion into the incision in the cystic duct and through the valves and other obstructions in the duct that may be encountered by the surgeon during the procedure. FIGS. 9A–9C show an embodiment 84 of the spoon-shaped head portion, including a lip 80b which is in the form of a flat bill shape. FIGS. 10A–10C show an embodiment 86 of the spoon-shaped head portion, including a lip 80c which is in the form of an extended flat bill shape. FIGS. 11A–11D show an embodiment 88 of the spoon-shaped head portion, including a lip 80d which is in the form of a pointed tip.

Figure 12A:
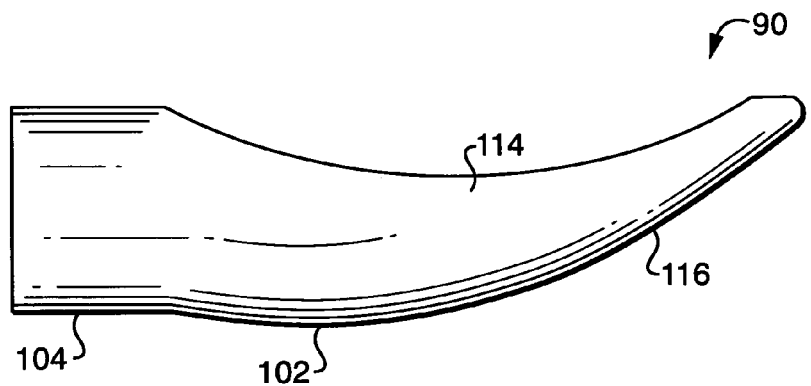
FIGS. 12A–12E are various views of another embodiment of a catheter introducer scoop-shaped head portion according to the present invention.
Figure 12B:
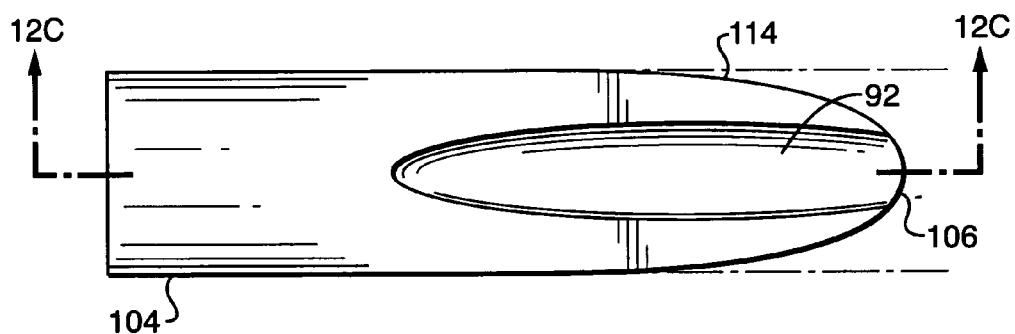
Figure 12C:
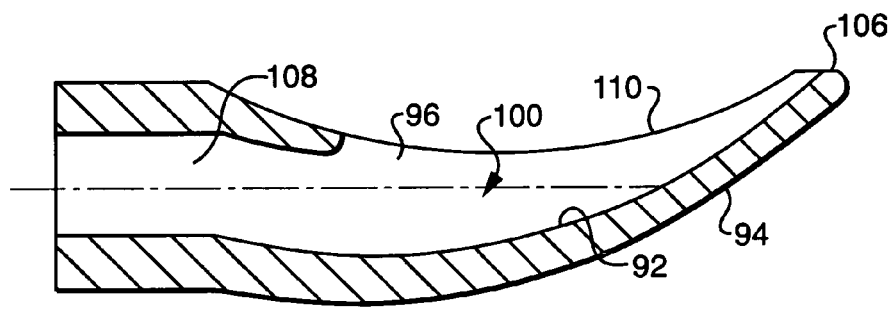
Figure 12D:
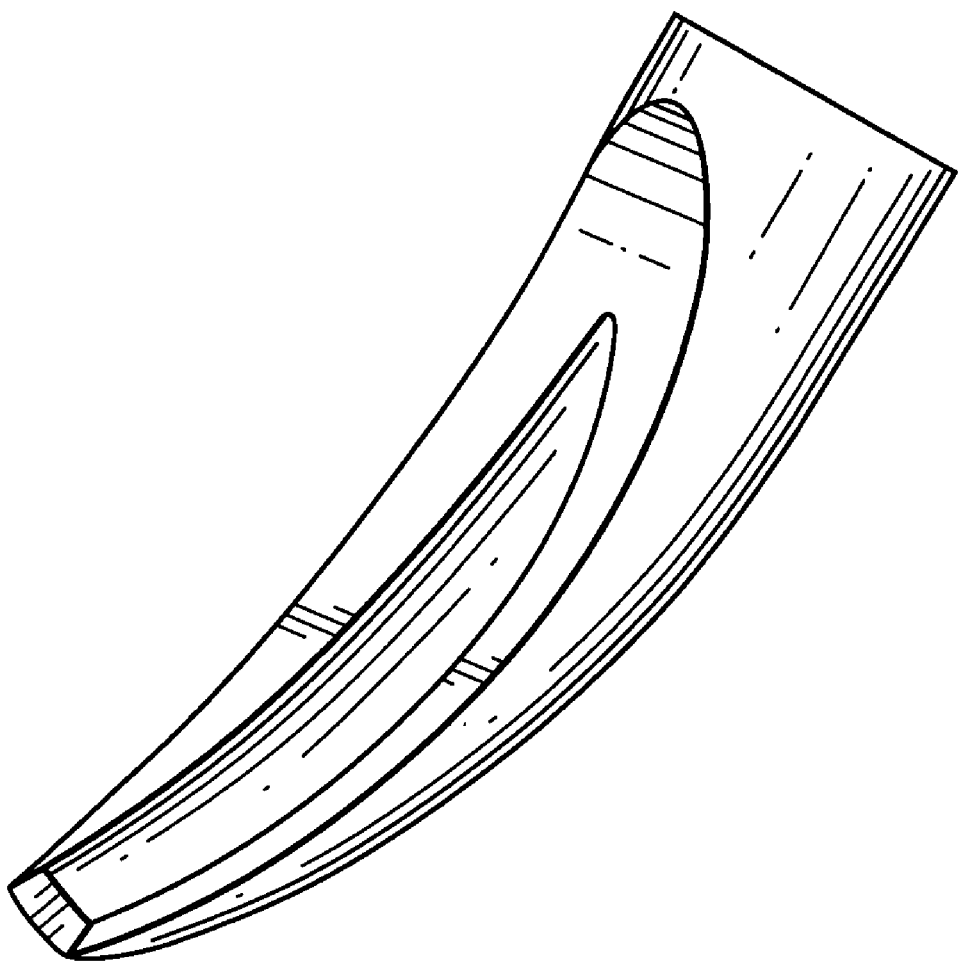
Figure 12E:
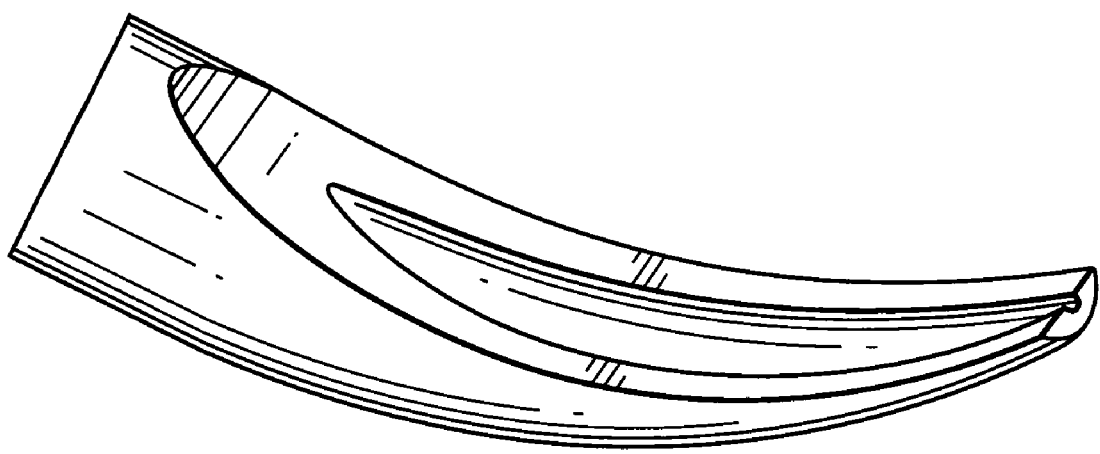

In yet another embodiment of the present invention, the head portion may be curved with respect to the longitudinal axis to enable the interior surface of the head portion to impart a deflecting force on the catheter as it is directed through the head portion and beyond the opening therein, however, with shallower side walls and a lower profile than the spoon-shaped head portion described above. FIGS. 12A–12D show such an embodiment 90, wherein FIG. 12A is a side view of the head portion 90, FIG. 12B is a top view of the head portion 90, FIG. 12C is a cross-sectional view of the head portion 90, taken along line 12C—12C in FIG. 12B and FIGS. 12D and 12E are three-dimensional perspective views of the head portion 90. As shown in FIGS. 12A–12E, head portion 90 is generally scoop-shaped, wherein interior surface 92 and the exterior surface 94 are curved upwardly with respect to the longitudinal axis 16. The combination of shallow sidewalls 96 and interior surface 92 result in a channel 100 that is concave in two-dimension, both along the longitudinal axis 16 and around it. This feature is particularly shown in FIGS. 12D and 12E.

As shown in FIGS. 12A–12E, the interior surface 92 and the exterior surface 94 converge toward each other to form a tip 106 which, as described above, is used to facilitate the insertion of the head portion 90 into an incision in the cystic duct. In the embodiment of head portion 90, channel 100 continuos until tip 106 with no lip between the channel 100 and tip 106. Lumen extension portion 108 of the head portion 90 terminates at an opening 110 of the head portion 90, which opening 110 enables a catheter passing through the lumen 14 and lumen extension portion 108 to exit the head portion proximate the tip 106 at an angle which is relatively acute with respect to the average plane within which the opening 110 lies. Similarly to the head portion 18, head portion 90 tapers from its proximal end 104, adjacent distal end 20 of tube 12 to the tip 106. This taper also occurs along outer sidewalls 114 as well as along exterior surface 116, the optional exception of portion 102, with respect to two orthogonal planes which intersect along the longitudinal axis 16 of tube 12.

Figure 13A:
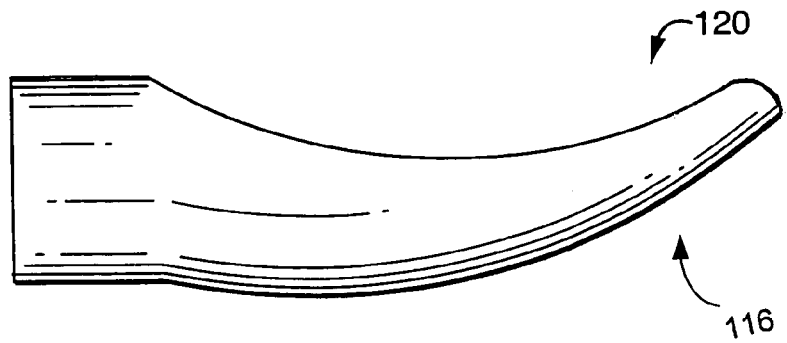
FIGS. 13A–13C are various views of another embodiment of a catheter introducer scoop-shaped head portion according to the present invention.
Figure 13B:
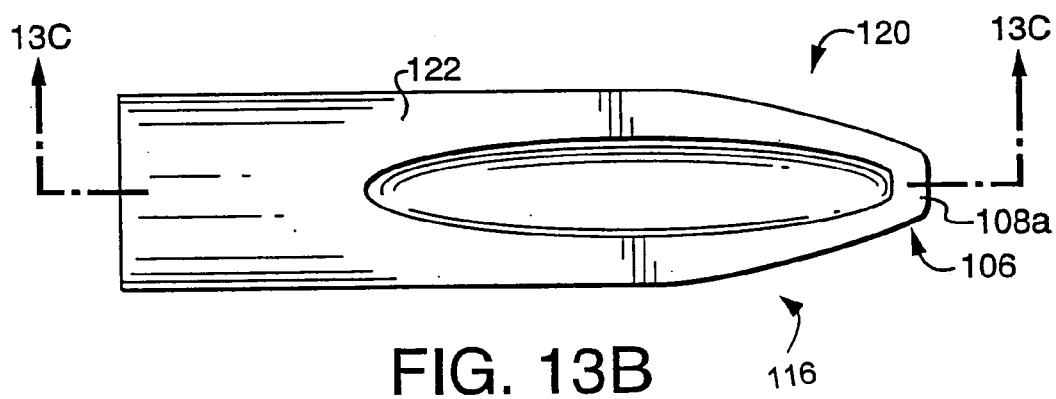
Figure 13C:
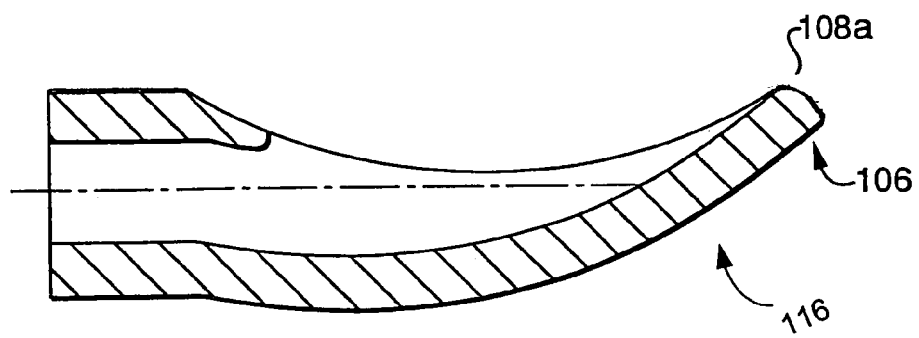

FIGS. 13A–13C show another embodiment 120 of the scoop-shaped head portion 18. This embodiment is similar to that shown in FIGS. 12A–12C, with the exception that the channel 100 terminates at a lip 108a of the tip 106. In this embodiment, lip 108a is formed to be continuous with exterior portion 122 of the head portion.

Figure 14A:
FIGS. 14A–14C are various views of another embodiment of a catheter introducer scoop-shaped head portion according to the present invention.
Figure 14B:
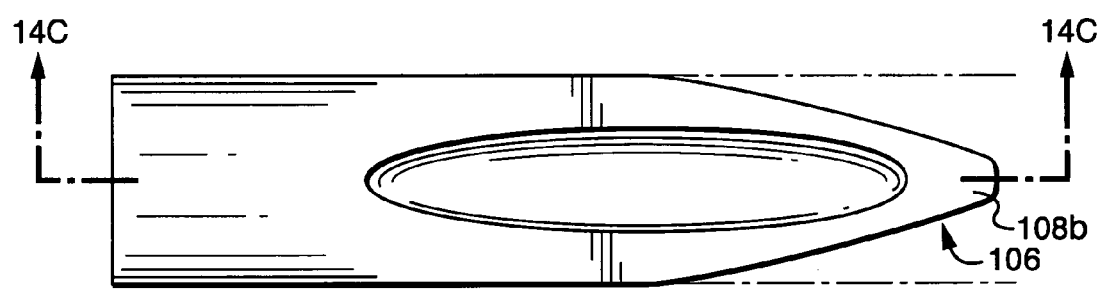
Figure 14C:
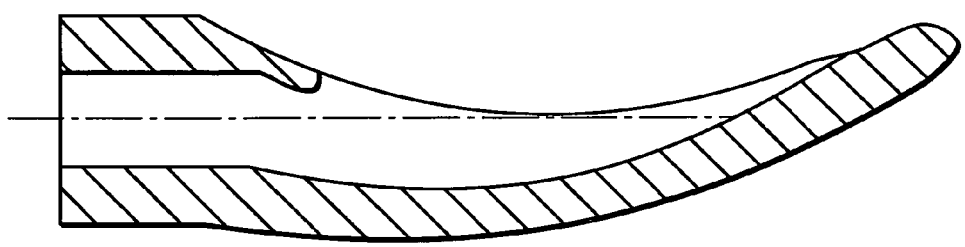
Figure 15A:
FIGS. 15A–15C are various views of another embodiment of a catheter introducer scoop-shaped head portion according to the present invention.
Figure 15B:
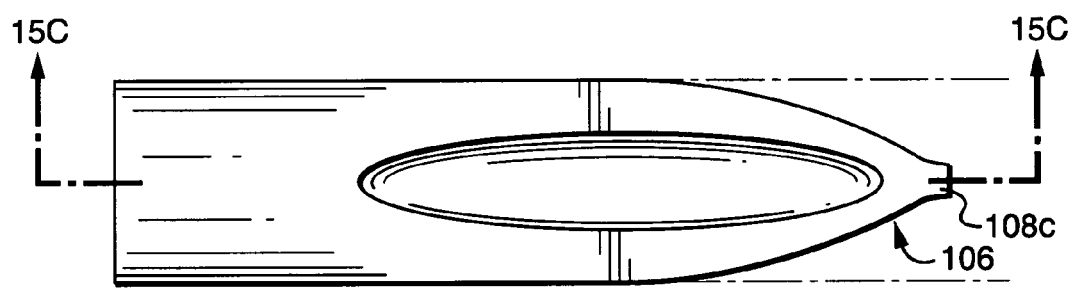
Figure 15C:
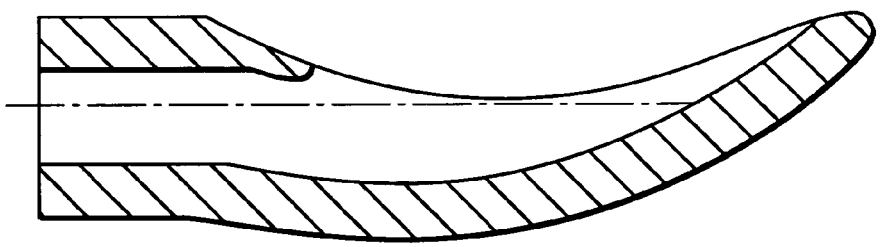
Figure 16A:
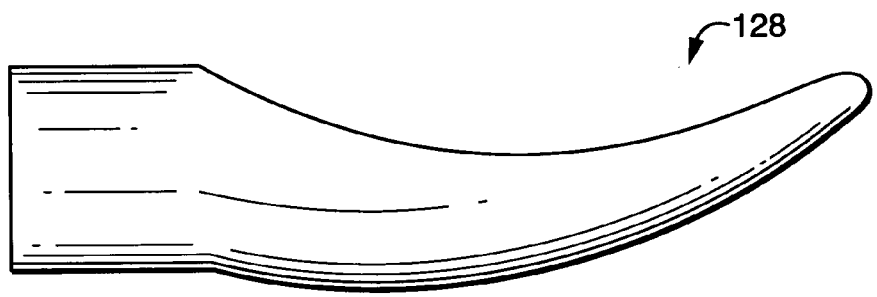
Figure 16B:
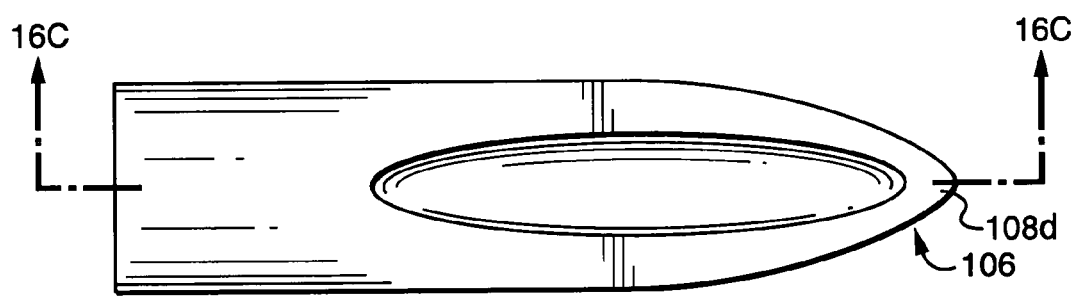
Figure 16C:
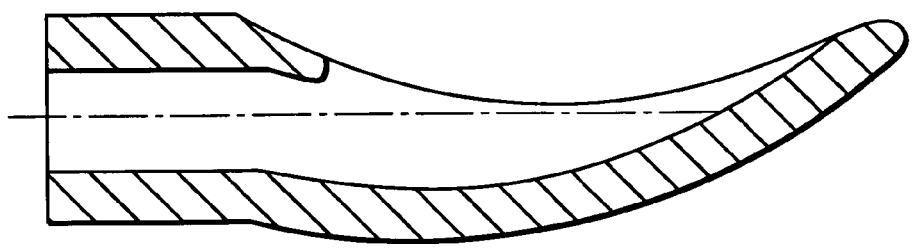

Shown in FIGS. 14–16 are various configurations of the lip 108. Each configuration is advantageous in enabling the surgeon to insert the tip and head portion into the incision in the cystic duct and through the valves and other obstructions in the duct that may be encountered by the surgeon during the procedure. FIGS. 14A–14C show an embodiment 124 of the scoop-shaped head portion, including a lip 108b which is in the form of a flat extended bill shape. FIGS. 15A–15C show an embodiment 126 of the scoop-shaped head portion, including a lip 108c which is in the form of an short flat bill shape. FIGS. 16A–16C show an embodiment 128 of the scoop-shaped head portion, including a lip 108d which is in the form of a pointed tip.

The head portion may be constructed such that the angle at which the catheter may exit the opening can vary from between approximately zero degrees, relative to the longitudinal axis, as shown in the embodiments of FIGS. 1–7, or at any angle up to approximately 90 degrees. With respect to the spoon and scoop-shaped head portions, the preferable range of the angle of exit of the catheter with respect to the longitudinal axis is approximately zero to approximately sixty degrees, and more preferably, between approximately zero and approximately thirty degrees.

The straight head, spoon-shaped head and scoop-shaped shaped head each have a suitably small profile. Preferably the straight head and spoon-shaped head portions are constructed such that they remain within planes which are tangent to the exterior surface of the tube 12. The smaller profile design of the protrusion allows insertion through the incision in the cystic duct, and placement within it. Following such insertion of the tip of the head portion, a catheter may be inserted into the introducer from the proximal end, and extended out from the opening in the head portion, and is guided into the lumen of the cystic duct. The curved, spoon-shaped and scoop-shaped designs of the head portion also provide lateral and longitudinal support for the catheter if it encounters resistance from valves or other obstructions.

The small profile design of the protrusion also makes it easier for the introducer to be inserted along the lumen of the cystic duct. During an operation, electro-cauterization may be utilized to stop any bleeding at the incision site, which may cause the duct tissue to shrink, or cause a buildup of dead tissue to obstruct the lumen of the cystic duct. The leading edge of the tip can be used to pass through this narrowed incision, and then can be positioned for navigating the catheter through the duct.

Figure 17:
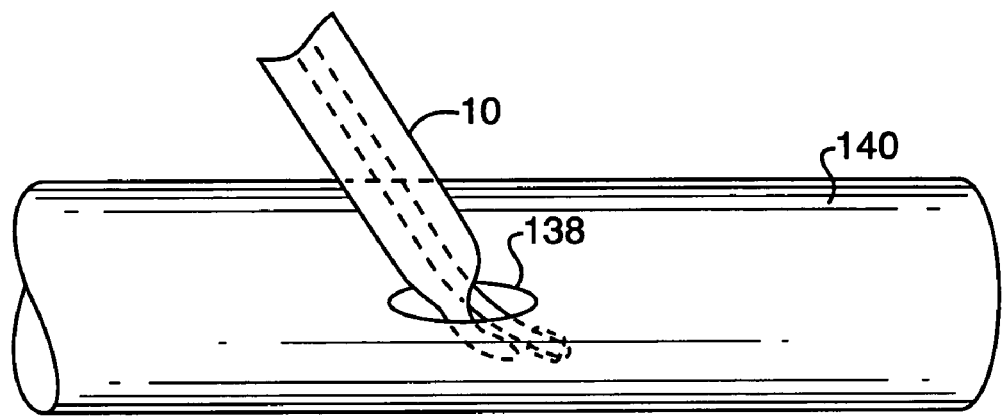
FIG. 17 is a top perspective view showing the catheter introducer of the present invention introducing a catheter into a cystic duct.
Figure 18:
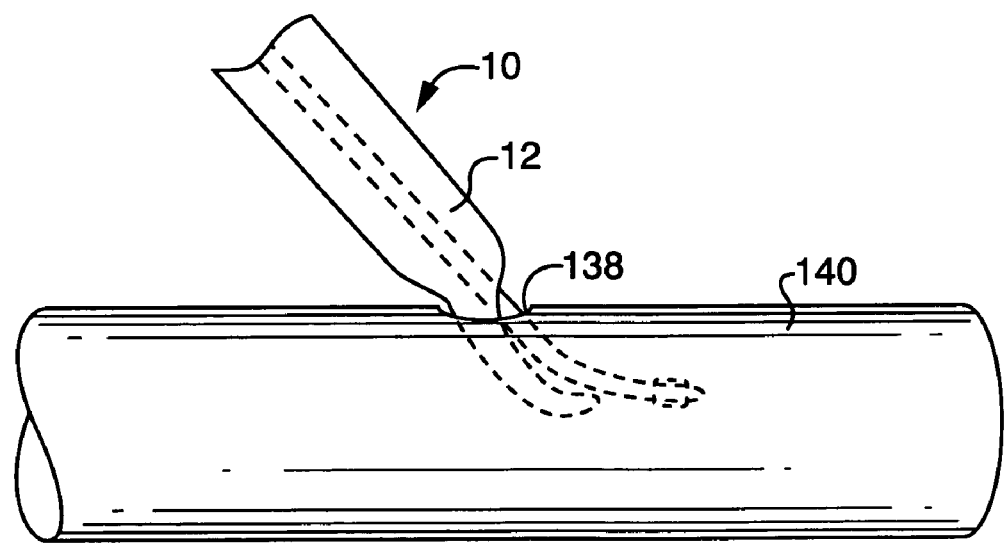
FIG. 18 is a side perspective view showing the catheter introducer of the present invention introducing a catheter into a cystic duct.

Referring to FIG. 17 and FIG. 18, which are top and side perspective views, respectively, of the insertion of the catheter introducer of the present invention into a cystic duct during an operation, the catheter introducer 10 is inserted by a surgeon through a trocar into a patient's abdomen. The introducer 10 is guided towards a transverse incision 138 in the cystic duct 140. In the case of the straight head portion, the head portion is then inserted into the incision in the duct, and positioned so that the longitudinal axis 16 of the tube generally lines up with the longitudinal axis of the duct, such that the catheter can be directed through the lumen and out of the straight head portion into the duct. In the case of the curved spoon and scoop-shaped head portions, the head portion is inserted into the incision in the duct, and positioned so that the concave channel is substantially perpendicular to the longitudinal axis of the duct. The catheter is then advanced through the introducer 10 until it extends to the concave channel and is then deflected laterally out of the opening in the head portion and is guided into the lumen of the duct substantially in line with the longitudinal axis of the duct. As described above, the positioning of the introducer 10 in the cystic duct provides good lateral and longitudinal support for the catheter if it encounters resistance from valves or other obstructions.

While the preferred embodiments and method of use of the invention have been illustrated and described in some detail in the drawings and foregoing description, it should be understood that this description is made only by way of example to set forth the best mode contemplated of carrying out the invention and not as a limitation to the scope of the invention which is pointed out by the claims below.

What is claimed is:

1. A catheter introducer comprising:
   a tube having a proximal end, a distal end and a lumen extending therethrough along a longitudinal axis of said tube for accommodating a catheter traveling along a longitudinal axis of said tube; and
   a head portion coupled to said distal end of said tube, said head portion including an aperture in fluid communication with said lumen at a proximal end thereof and a tip at a distal end thereof, an exterior surface extending from said proximal end thereof to an opening of said head portion along a first portion of said head portion and extending from said proximal end thereof to said tip along an opposing portion of said head portion and an interior surface extending from said aperture to said opening of said head portion along said first portion of said head portion and extending from said aperture toward said tip along said opposing portion of said head portion;

wherein said opening is bounded to establish a smooth concave side profile;

wherein said exterior surface circumferentially tapers from a head proximal portion to said distal end of said head portion;

wherein walls defining the head portion have substantially constant thickness, and the distal tip of the head portion is offset with respect to the longitudinal axis;

wherein said tip of said head portion is within planes which are tangent to an outer surface of said tube at the distal end of said tube; and said interior surface forms a channel for receiving a catheter passing through said lumen and said aperture, said channel being concave along at least one axis.

2. The catheter introducer of claim 1 wherein said interior surface is curved along a radius of curvature.

3. The catheter introducer of claim 2 wherein said radius of curvature is a nonzero value.

4. The catheter introducer of claim 3 wherein said channel deflects the catheter from traveling along said longitudinal axis to a direction oblique to said longitudinal axis as the catheter is directed through said head portion.

5. The catheter introducer of claim 2 wherein said head is constructed such that the catheter exits said opening at an angle which is between zero and thirty degrees with respect to the longitudinal axis.

6. The catheter introducer of claim 1 wherein said channel is concave along two axes.

7. The catheter introducer of claim 1 wherein said exterior surface along said first portion of said head portion completely surrounds said opening, thereby forming a protruding portion at said tip.

8. The catheter introducer of claim 7 wherein said protruding portion comprises a flat bill.

9. The catheter introducer of claim 7 wherein said protruding portion comprises a pointed tip.

10. The catheter introducer of claim 1 wherein said head portion is constructed such that the longitudinal axis of said tube intersects said channel.

11. The catheter introducer of claim 1 wherein a line connecting said first portion of said exterior surface at said opening and said tip lies in a plane which is oblique with respect to said longitudinal axis.

12. The catheter introducer of claim 1 further including a catheter.

13. A catheter introducer comprising:

a tube extending along a longitudinal axis having an outer generally cylindrical surface and an interior surface defining a central lumen for accommodating a catheter, said tube including an open-faced head portion extending along said longitudinal axis from a distal end of said tube, wherein said head portion includes an upper surface in connection with said lumen, a lower surface extending from said outer surface of said tube, a distal tip, and a catheter receiving portion formed between said lumen and said tip, said catheter receiving portion being defined by an at least one axis concave surface extending from the interior surface of central lumen to the distal tip;

wherein said upper surface and said lower surface extend to said distal tip;

wherein walls defining the head portion have substantially constant thickness, and the distal tip of the head portion is offset with respect to the longitudinal axis;

wherein said tip of said head portion is within planes which are tangent to an outer surface of said tube at the distal end of said tube; and wherein said head portion is tapered at least from a point between said distal end of said tube and said distal tip along said longitudinal axis in at least one plane; and wherein said open faced head portion is bounded to establish a smooth concave side profile.

14. The catheter introducer of claim 13 wherein said tip is pointed.

15. The catheter introducer of claim 13 wherein said tip is flat.

16. The catheter introducer of claim 13 wherein said tip is channeled.

17. The catheter introducer of claim 13 wherein said head portion has a width, which decreases monotonically from the distal end of the tube to the distal tip of thereof.

18. The catheter introducer of claim 13 wherein said head portion has a width, which monotonically decreases from a point between the distal end of the tube and the distal tip of the head portion to the distal tip of the head portion.

19. The catheter introducer of claim 13 wherein said head portion is scoop-shaped with respect to a longitudinal axis of said tube.

20. A kit comprising the catheter introducer of claim 13 and a catheter.

* * * * *